United States Patent
Brennan

(10) Patent No.: US 9,480,827 B2
(45) Date of Patent: Nov. 1, 2016

(54) DRAINAGE CANNULA WITH ANCHOR TAB

(71) Applicant: H. George Brennan, Newport Beach, CA (US)

(72) Inventor: H. George Brennan, Newport Beach, CA (US)

( * ) Notice: Subject to any disclaimer, the term of this patent is extended or adjusted under 35 U.S.C. 154(b) by 0 days.

(21) Appl. No.: 13/828,442

(22) Filed: Mar. 14, 2013

(65) Prior Publication Data

US 2014/0276653 A1  Sep. 18, 2014

(51) Int. Cl.
*A61M 27/00* (2006.01)
*A61M 25/02* (2006.01)

(52) U.S. Cl.
CPC ............ *A61M 27/00* (2013.01); *A61M 25/02* (2013.01); *A61M 2025/0286* (2013.01)

(58) Field of Classification Search
CPC ............ A61M 27/00; A61M 1/0023; A61M 2025/0253; A61M 2025/0213; A61M 2025/024; A61M 2025/0266; A61M 2025/026; A61M 2025/0286
USPC .................................. 604/180, 232
See application file for complete search history.

(56) References Cited

U.S. PATENT DOCUMENTS

| | | | |
|---|---|---|---|
| 4,500,311 A | 2/1985 | Redmond et al. | |
| 4,573,965 A * | 3/1986 | Russo | 604/30 |
| 5,364,367 A * | 11/1994 | Banks et al. | 604/174 |
| 5,382,239 A * | 1/1995 | Orr | A61M 25/02 604/177 |
| 5,683,378 A * | 11/1997 | Christy | 606/1 |
| 5,776,111 A * | 7/1998 | Tesio | 604/264 |
| 2003/0018309 A1 | 1/2003 | Breznock | |
| 2006/0025723 A1 * | 2/2006 | Ballarini | 604/180 |
| 2007/0083189 A1 | 4/2007 | Lampropoulos et al. | |
| 2007/0282309 A1 * | 12/2007 | Bengtson | A61M 1/0088 604/541 |
| 2008/0243082 A1 * | 10/2008 | Goodman | 604/180 |

FOREIGN PATENT DOCUMENTS

WO  WO9304726  3/1993

OTHER PUBLICATIONS

University of Saskatchewan, "6. Chinese Finger Knot (Roman Sandal Tie)", web page and video, http://emap-projects.usask.ca/vsac205/Lab3/lab/lab3_1.3.3.php#fingerknot_movie, 1994-2009, 1 page.
International Search Report and Written Opinion for International Application No. PCT/US2014/018758; May 22, 2014; 9 pages.

* cited by examiner

*Primary Examiner* — Leslie Deak
*Assistant Examiner* — Kai Weng
(74) *Attorney, Agent, or Firm* — Stetina Brunda Garred and Brucker

(57) ABSTRACT

A drainage cannula having one of three different types of anchor tabs is disclosed. The anchor tab prevents movement of the cannula after positioning a distal portion of the cannula inside of the patient's body and securing the anchor tab to the patient's body (e.g., skin).

9 Claims, 3 Drawing Sheets

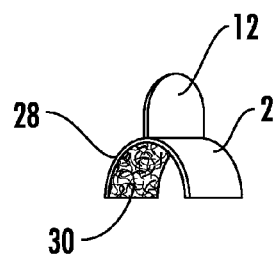
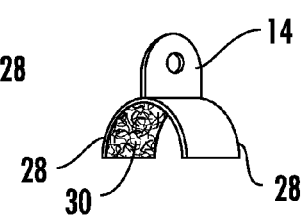
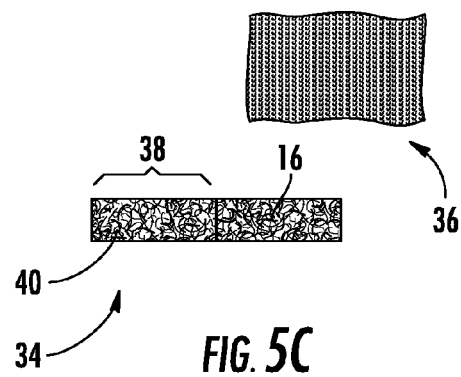
FIG. 5A    FIG. 5B    FIG. 5C
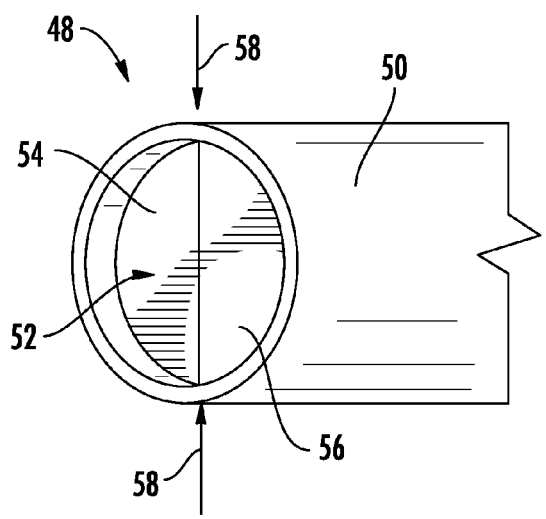
FIG. 6

DRAINAGE CANNULA WITH ANCHOR TAB

CROSS-REFERENCE TO RELATED APPLICATIONS

Not Applicable

STATEMENT RE: FEDERALLY SPONSORED RESEARCH/DEVELOPMENT

Not Applicable

BACKGROUND

The various embodiments disclosed herein relate to a drainage cannula with an anchor tab.

After surgery, a dead space within the patient's body is typically created. Bodily fluid is aggregated within this dead space and must be drained to prevent infections and collection of bodily fluids which will require evacuation. To this end, a drainage cannula is inserted into a patient's body to drain the bodily fluid from the patient. A portion of the cannula is disposed inside the patient's body under the skin while another portion of the cannula is disposed outside the patient's body. Bodily fluid created within the patient's body flows out of the cannula into a reservoir for disposal at a later time. Unfortunately, the cannula is capable of shifting and the apertures formed on the cannula disposed within the body can be exposed to the environment. In this unfortunate event, bodily fluid will leak out of those apertures exposed to the environment and create sanitary issues. Moreover, the portion of the cannula that was previously disposed within the body and is now exposed to the environment is now contaminated. One cannot merely reinsert or push the cannula back into the patient's body. Otherwise, the exposed and contaminated portion of the cannula would cause an infection in the patient's body. Another problem of the prior art drainage cannula is that one of the apertures formed on the proximal side may become exposed to the atmosphere. In this case, the closed vacuum suction being used to draw bodily fluid from the patient to a reservoir would lose suction and prevent the withdrawal of bodily fluid from the patient. As discussed previously, the cannula cannot be merely reinserted or pushed into the patient's body due to contamination of the exposed portion of the drainage cannula. Instead, the exposed aperture may be covered with tape to reestablish the vacuum in the drainage cannula. If the drainage cannula shifts a significant distance so that a significant number of apertures are now exposed to the environment or the apertures are no longer properly positioned within the patient's body, the doctor must reestablish the drain. To do so, the patient must be anesthetized, opened up and the drainage cannula repositioned.

In order to prevent the drainage cannula from shifting out of the patient's body, complex suturing methods are used in an attempt to secure the drainage cannula in position. In particular, a series of sutures are made on the exposed portion of the drainage cannula that ties the exposed portion of the drainage cannula to the skin of the patient. Unfortunately, this does not provide proper securement of the drainage cannula and still allows the drainage cannula to shift out of the patient's body.

Accordingly, there is a need in the art for an improved drainage cannula which can be easily secured in a desired position within/upon a patient to prevent unintentional cannula shifting.

BRIEF SUMMARY

The drainage cannula with anchor tab disclosed herein addresses the needs discussed above, discussed below and those that are known in the art.

The drainage cannula disclosed herein has one of three different types of anchor tabs. The first type of anchor tab is a puncturable anchor tab that is secured to a proximal portion which remains exposed to the environment while the distal portion of the drainage cannula remains inserted inside of the patient's body. The puncturable tab is punctured with a needle and thread to suture the puncturable tab to the patient's body after positioning the drainage cannula in the patient's body. The second type of anchor tab is a tab having a preformed hole formed there through. In this manner, the needle does not need to puncture through the tab. Rather, the needle is inserted through the through hole of the tab and sutured to the patient's body. The third type of anchor tab includes first and second parts that form a fastening system. The first and second parts are removably attachable to each other. The first part is attached to the proximal portion of the cannula. The second part is attached to the patient's body. After inserting the cannula into the patient's body and positioning the apertures formed on the distal portion of the cannula at the proper position where the bodily fluid is being generated, the first and second parts are attached to each other to prevent movement of the cannula while draining bodily fluid.

More particularly, a drainage cannula securable to mitigate inadvertent movement is disclosed. The cannula may comprise an elongate hollow tube and a means for securing a proximal portion of the tube to a body of a patient. The elongate hollow tube may have a distal portion and a proximal portion. The distal portion may have an aperture for aspirating bodily fluid and a proximal portion disposed outside of a body during use. The means for securing the proximal portion to the body may be attached to the proximal portion.

The means for securing may be a puncturable tab extending out of the proximal portion. The puncturable tab may be flexible or rigid. Alternatively, the means for securing may be a tab extending out of the proximal portion. This tab may have a hole therethrough. This tab may be flexible or rigid. Alternatively, the means for securing may have first and second parts which are removable securable to each other. The first and second parts of the means for securing may be hooks and loops.

The distal portion of the cannula may have a plurality of apertures.

In another aspect, a method of draining bodily fluid from a body in a secure manner is disclosed. The method comprising the steps of inserting a distal portion of a drainage cannula into an opening in the body with an aperture formed in the distal portion disposed within the body; closing the opening in the body; and step for securing a proximal portion of the drainage cannula to the body.

The closing step may include the step of suturing the opening in the body to close the opening in the body.

The step for securing may include the step of puncturing a tab extending from the proximal portion of the cannula with a thread and suturing the tab to the body. Alternatively, the step of securing may include the step of threading a suture through a hole in a tab extending from the proximal portion of the cannula with a thread and suturing the tab to the body. Alternatively, the step of securing may include the step of securing a first part of a two part removably attachable mechanism to the body and securing the first part to a second part of the two part removably attachable mechanism which is attached to the proximal portion.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 5A is a perspective view of the first embodiment of the anchor tab fabricated as a separate retrofit anchor tab;

FIG. 5B is a perspective view of the second embodiment of the ancho tab fabricated as a separate retrofit anchor tab;

FIG. 5C is a perspective view of the third embodiment of the anchor tab fabricated as a separate retrofit anchor tab; and FIG. 6 is a perspective view of a tube with an internal valve.

DETAILED DESCRIPTION

Figure 1:
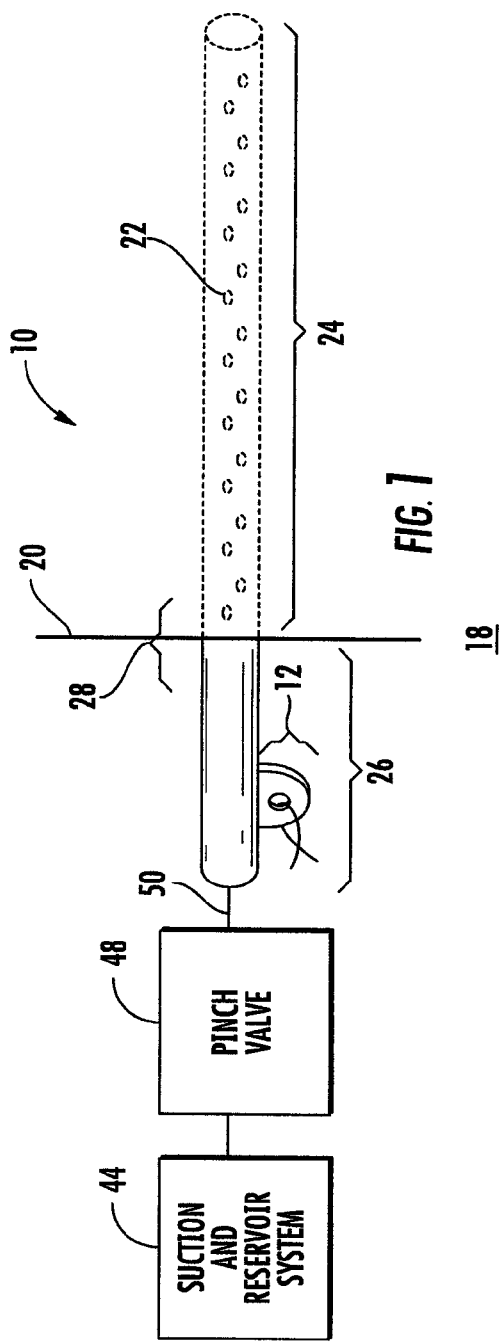
FIG. 1 is a perspective view of a drainage cannula illustrating a first embodiment of an anchor tab.

Referring now to the drawings, a drainage cannula 10 with anchor tabs 12, 14, 16 is shown. The anchor tabs 12, 14, 16 are easily securable to the patient to prevent the drainage cannula 10 from shifting after placement in the body 18 of the patient. In this manner, the drainage cannula 10 will not inadvertently shift or dislodge from the patient's body upon movement of the patient. As a result, there is no opportunity for the apertures 22 formed on the distal portion 24 of the cannula 10 to slip out and become exposed to the ambient air environment thereby causing a leak of bodily fluid. The benefit of such configuration provides more mobility to the patient and facilitates more efficient and sanitary drainage of bodily fluid from the patient.

More particularly, referring now to FIG. 1, the drainage cannula 10 is shown positioned within the patient's body for draining bodily fluid. In particular, the patient's body 18 has an opening 20. The drainage cannula 10 is inserted through the opening 20 and positioned within the patient's body 18 so that all of the apertures 22 formed on the distal portion 24 are disposed within the patient's body 18. A proximal portion 26 of the cannula 10 is exposed to the environment and protrudes out of the opening 20.

The proximal portion 26 of the cannula 10 incorporates an anchor tab 12. This anchor tab 12 is securable to the patient with a suture. The anchor tab 12 may be fabricated from a material that can be punctured with a needle. By way of example and not limitation, the anchor tab 12 may be fabricated from a plastic material, metallic material and other materials known in the art and developed in the future.

Figure 2:
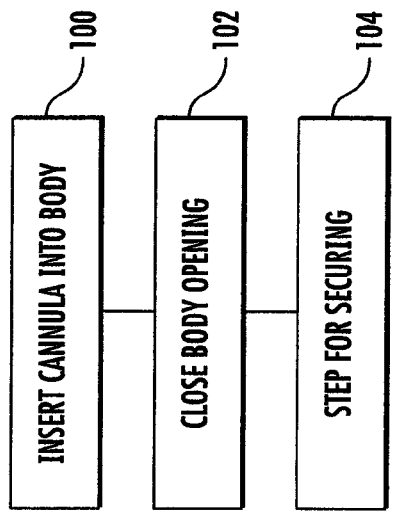
FIG. 2 is a flow chart of utilizing the drainage cannula with anchor tab.

In use, a medical professional will insert the cannula 10 shown in FIG. 1 into the opening 20 of the patient's body. The cannula 10 is inserted 100 (see FIG. 2) until all the apertures 20 of the distal portion 24 of the cannula 10 are disposed within the patient's body. Moreover, the apertures 20 are positioned so as to be effective at draining bodily fluid from a local area of the patient's body that needs to be drained. Next, the body opening 20 is closed 102 by methods known in the art or developed in the future. By way of example and not limitation, the body opening 20 may be closed with a medical grade sealant or suturing. Thereafter, a step for securing the cannula 10 to the patient's body to prevent movement of the cannula 10 while draining bodily fluid from the patient's body 18 is performed. The step for securing the cannula 10 as shown in FIG. 1 includes the step of suturing the anchor tab 12 to the skin of the patient. To this end, the anchor tab 12 being fabricated from a punctureable material is punctured with a needle having a thread. The medical professional sutures the tab 12 to the skin of the patient which limits movement of the cannula 10 so that the apertures 22 formed on the distal portion 24 of the cannula 10 are not exposed to the environment.

Figure 3:
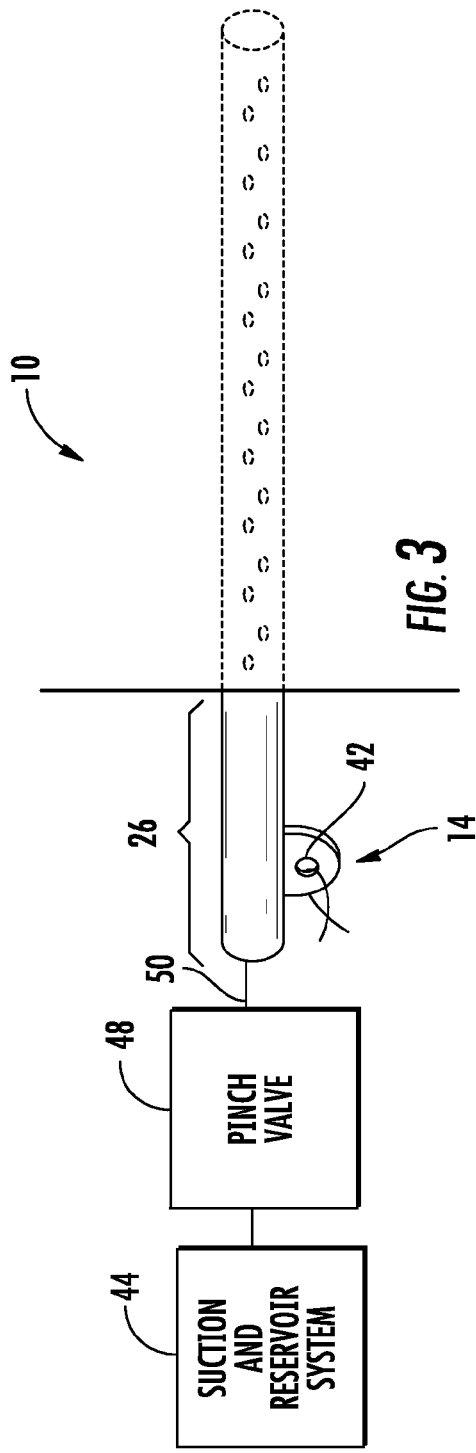
FIG. 3 is a perspective view of the drainage cannula illustrating a second embodiment of the anchor tab.

Referring now to FIG. 3, a cannula 10 with a different type of tab 14 is shown. The tab 14 is attached to the proximal portion 26 of the cannula 10. The tab 14 may be identical to tab 12 discussed in relation to FIG. 1 except that the tab 14 has an aperture 42 so that the medical professional does not need to pierce the tab 14 with a needle to suture the tab 14 to the patient's body. In this embodiment, the step for securing the cannula includes the step of threading a needle and thread into the aperture 42 and suturing the tab 14 to the patient's body.

Figure 4:
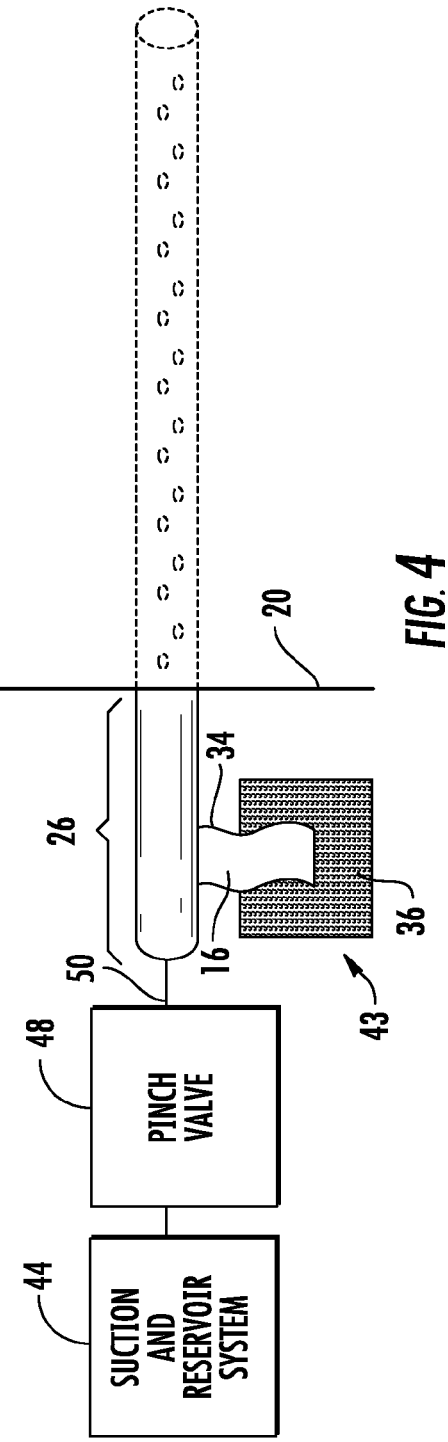
FIG. 4 is a perspective view of the drainage cannula illustrating a third embodiment of the anchor tab.

Referring now to FIG. 4, a tab 16 is shown. The tab 16 extends from the proximal portion 26 of the cannula 10. The tab 16 is part of a two-cart fastening system, namely, a hooks and loops fastening system. One or both sides of the tab 16 has the first part 34 of the hooks and loops fastening system. A patch 43 has the second part 36 of the hooks and loops fastening system. The patch 43 may be secured to the patient's body adjacent to the opening 20. Patch 43 may be secured to the patient's body by way of adhesive or suturing or other methods known in the art or developed in the future. In this embodiment, the step for securing the cannula includes the step of securing the patch 43 to the patient's body and securing the first and second parts of the hooks and loops fastening system to each other.

Although the tab 16 has been described in relation to a hooks and loops fastening system, it is contemplated that the tab 16 may be incorporated into a two (2) part fastening system such as snaps or other two (2) part fastening systems known in the art or developed in the future.

Although the process of utilizing the drainage cannula 10 with anchor tabs 12, 14, 16 has been described with the step for securing 104 as being performed after closing the body opening 102, it is also contemplated that the step for securing 104 may be performed before the step of closing the body opening 102.

Each of the embodiments of the cannula 10 shown in FIGS. 1, 3 and 4 is shown as being straight. However, it is also contemplated that the cannula 10 may be bent so that the distal portion 24 may be positioned deep beneath the skin of the patient's body 18 while the proximal portion 26 lays generally flat upon the skin of the patient's body 18. The bend formed in the cannula 10 may occur at the transition region 28 between the distal portion 24 and the proximal portion 26 of the cannula 10. Additionally or alternatively, the bend formed in the cannula 10 may occur at a portion of the length of the cannula 10. By way of example and not limitation, the distal portion 24 and/or the proximal portion 26 may be curved.

The cannula 10 shown in FIGS. 1, 3 and 4 may be fabricated from a metallic material and be substantially rigid. However, it is also contemplated that the cannula 10 may be fabricated from a generally flexible material such as plastic. In each of these cases, the tabs 12, 14 and 16 may be attached to the proximal portion 26 of the cannula 10 by one or more methods. By way of example and not limitation, the tabs 12, 14, 16 may be fabricated as a separate component from the cannula 10, as shown in FIGS. 5A-5C. In particular, the tabs 12 and 14 may have a film 28 with a pressure sensitive adhesive 30 disposed underneath the film 28. To utilize the tabs 12 and 14, the film 28 is adhered to the proximal portion 20 of the cannula 10. Thereafter, the tabs 12 and 14 may be secured to the patient as discussed above. In certain instances, the tabs 12 and 14 may be fabricated so as to be integral with the cannula 10. By way of example and not limitation, the tabs 12 and 14 if fabricated from a plastic material may be formed during an injection molding process used to form the cannula 10. In this manner, no after work is required to attach the tabs 12, 14 to the cannula. The same may be true if the cannula 10 is fabricated from a metallic material. The tabs 12, 14 may be formed by the same process as the cannula 10 during manufacture of the cannula 10.

The tab 16 shown in FIG. 5C illustrates a first and second part 34, 36 of a hooks and loops fastening system. The first and second parts 34, 36 may be hooks and loops, respectively or vice versa loops and hooks, respectively. Preferably, the second part 36 is hooks. The distal portion 38 of the first part 34 of the hook and loop system may have a pressure sensitive adhesive 40 which is used to secure the first part 34 to the proximal portion 26 of the cannula 10. The second part 36 may be secured to the cannula 10 shown in FIGS. 1, 3 and 4 and have a plurality of apertures 22 formed on the distal portion 24 of the cannula 10. Although a plurality of apertures 22 are shown, it is also contemplated that the carmula 10 may have a limited number of apertures 22 and may even have a single aperture at the distal end 30 of the cannula 10. These apertures 22 are positioned at the locations within the patient's body where bodily fluid is being produced and must be drained.

In each of the three embodiments discussed herein, the cannula 10 may be fluidically attached to a suction and reservoir system 44. In particular, the proximal portion 26 of the cannula 10 has an opening which is connected to a tube. The tube is connected to a vacuum pump (e.g., mechanical pump or bulb system) which creates a vacuum to draw bodily fluid from the patient's body to a reservoir.

The above description is given by way of example, and not limitation. Given the above disclosure, one skilled in the art could devise variations that are within the scope and spirit of the invention disclosed herein, including various ways of fabricating the cannula. Further, the various features of the embodiments disclosed herein can be used alone, or in varying combinations with each other and are not intended to be limited to the specific combination described herein. Thus, the scope of the claims is not to be limited by the illustrated embodiments.

The suction and reservoir system 44 may be a suction bulb. The suction bulb creates suction within the drainage cannula 10 to withdraw bodily fluid from the patient's body due to the resiliency of the suction bulb. The suction bulb is initially depressed and a tube from the drainage cannula 10 is connected to the suction bulb. The resiliency of the material from which the suction bulb is made expands the suction bulb to create a vacuum which draws the bodily fluid from the patient's body into the suction bulb. After a period of time, the suction bulb will have expanded and provide minimal suction and be incapable of withdrawing bodily fluid from the patient's body. Additionally, the suction bulb acts as a reservoir and may be full of bodily fluid. In this event, it is advisable to drain the suction bulb or replace the suction bulb with a new suction bulb. In either instance, the suction bulb must be disconnected from the tube. In disconnecting the suction bulb from the tube, the bodily fluid in the tube may leak and cause sanitary issues for the medical professional or patient changing out the old bulb. To prevent leakage of the bodily fluid within the tube, a pinch valve 48 may be incorporated into the tube 50. The pinch valve may have an internal mechanism by which flow of bodily fluid within the tube 50 may be shut or open. For example, as shown in FIG. 6, the tube 50 may have an internal valve 52 defined by first and second flats 54, 56. The pinch valve 48 may incorporate a mechanical system by which opposed forces 58 deform the tube 50. Upon deformation under the force of opposed forces 58, the first and second flaps 54, 56 open up and allow bodily fluid to flow therethrough. To change out the bulb, the mechanical system for applying the opposed forces 58 are removed so that the first and second flaps 54, 56 remain closed as shown in FIG. 6. The pinch valve 48 may also be an external mechanical system by which fluid flowing through the tube 50 is stopped. To this end, the pinch valve 48 may be a cam action lever having a stopped position and an open position wherein fluid flowing through the tube 50 is stopped when the cam action lever is in the stopped position and fluid flowing through the tube 50 is allowed to continue when the cam action lever is in the open position.

The system and method described herein in relation to the drainage cannula 10 with anchor tabs 12, 14, 16 benefits the doctor in that the doctor does not have to open up the patient and reestablish the drainage cannula. Additionally, it is easier for the caregiver to address the patient's needs in changing out the suction bulb and provide for a more sanitary condition. Additionally, the patient benefits because the patient does not need to go through another procedure and can live under sanitary conditions. Moreover, the patient's ability to heal is further facilitated by use of the drainage cannula 10 with anchor tabs 12, 14, 16 disclosed herein.

The above description is given by way of example, and not limitation. Given the above disclosure, one skilled in the art could devise variations that are within the scope and spirit of the invention disclosed herein, including various ways of fabricating the cannula. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A drainage cannula for removal of bodily fluid from a wound site during outpatient care and securable to a body to eliminate inadvertent movement to prevent contamination and loss of suction, the cannula comprising:

a single lumen elongate hollow flexible aspiration tube defining a longitudinal axis, the elongate hollow flexible aspiration tube having a distal portion and a proximal portion, the distal portion disposable within the wound site and having a plurality of apertures for aspirating bodily fluid from the wound site and the proximal portion configured to be disposed outside of the body during use;

a pinch valve attached to the proximal portion of the elongate hollow flexible aspiration tube to prevent leakage of bodily fluid;

a flat anchor tab permanently attached to the elongate hollow flexible aspiration tube, the flat anchor tab defining a plane with the flat anchor tab oriented so that the plane is parallel to the longitudinal axis, the flat anchor tab extending outward from an outer surface of the elongate hollow flexible aspiration tube for securing the proximal portion to the body adjacent the wound site with the proximal portion of the elongate hollow flexible aspiration tube laid flat against the skin of a patient and eliminating movement of the elongate hollow flexible aspiration tube into or out of the wound site;

wherein the proximal portion of the elongate hollow flexible aspiration tube is laid flat against the skin of the body and the flat anchor tab is parallel and secured to the skin of the body during use;

wherein the flat anchor tab and flexible tube are bendable to fit a contour of the skin;

a suction bulb attachable to the proximal portion of the elongate hollow flexible aspiration tube to establish vacuum communication between the suction bulb and the elongate hollow flexible aspiration tube.

2. The cannula of claim 1 wherein the anchor tab comprises a puncturable tab extending out from the proximal portion.

3. The cannula of claim 1 wherein the anchor tab comprises a tab extending out from the proximal portion and having a hole therethrough.

4. The cannula of claim 1 wherein the anchor tab comprises a first part of a hook and loop fastening system, and a second part of the hook and loop fastening system is secured to the skin of the body, the first and second parts being removably securable to each other.

5. The cannula of claim 4 wherein the first and second parts are respectively loops and hooks.

6. The cannula of claim 3 wherein the tab is rigid.

7. The cannula of claim 1 wherein the distal portion has a plurality of apertures for aspirating bodily fluid from the wound site.

8. A drainage cannula for removal of bodily fluid from a wound site and securable to a body to eliminate inadvertent movement to prevent contamination during outpatient care and loss of suction, the cannula comprising:

a single lumen elongate hollow flexible aspiration tube defining a longitudinal axis, the single elongate hollow flexible tube having a distal portion and a proximal portion, the distal portion disposable within the wound site and having a plurality of apertures for aspirating bodily fluid from the wound site and the proximal portion configured to be disposed outside of the body during use;

a pinch valve attached to the proximal portion of the single elongate hollow flexible aspiration tube to prevent leakage of bodily fluid; and a flat anchor tab permanently attached to the single elongate hollow flexible aspiration tube, the flat anchor tab defining a plane with the flat anchor tab oriented so that the plane is parallel to the longitudinal axis, the flat anchor tab extending outward from an outer surface of the single elongate hollow flexible tube for securing the proximal portion to the body adjacent the wound site with the proximal portion of the single elongate flexible tube laid flat against the skin of a patient and eliminating movement of the single elongate hollow aspiration tube into or out of the wound site;

a suction bulb attachable to the proximal portion of the single elongate hollow flexible aspiration tube to establish vacuum communication between the suction bulb and the aspiration tube;

wherein the proximal portion of the single elongate hollow flexible tube is laid flat against the skin of the body and the flat anchor tab is parallel and secured to the skin of the body during use.

9. A drainage cannula for removal of bodily fluid from a wound site during outpatient care and securable to a body to eliminate inadvertent movement to prevent contamination and loss of suction, the cannula comprising:

a single lumen elongate hollow flexible aspiration tube defining a longitudinal axis, the single elongate hollow flexible aspiration tube having a distal portion and a proximal portion, the distal portion disposable within the wound site and having a plurality of apertures for aspirating bodily fluid from the wound site and the proximal portion configured to be disposed outside of the body during use;

a pinch valve attached to the proximal portion of the single elongate hollow flexible aspiration tube to prevent leakage of bodily fluid;

a flat anchor tab permanently attached to the single elongate hollow flexible aspiration tube, the flat anchor tab defining a plane with the flat anchor tab oriented so that the plane is parallel to the longitudinal axis, the flat anchor tab extending outward from an outer surface of the single elongate hollow flexible aspiration tube for securing the proximal portion to the body adjacent the wound site with the proximal portion of the single elongate hollow flexible aspiration tube laid flat against the skin of a patient and eliminating movement of the single elongate hollow flexible aspiration tube into or out of the wound site;

wherein the proximal portion of the elongate hollow flexible aspiration tube is laid flat against the skin of the body and the flexible flat anchor tab is parallel and secured to the skin of the body during use;

a suction bulb attachable to the proximal portion of the single elongate hollow flexible aspiration tube to establish vacuum communication between the suction bulb and the aspiration tube;

wherein the flat anchor tab and single elongate hollow flexible aspiration tube are bendable to fit a contour of the skin.

* * * * *